United States Patent [19]
Christodoulou et al.

[11] Patent Number: 5,389,675
[45] Date of Patent: Feb. 14, 1995

[54] MIXED LIGAND METAL COMPLEXES OF NITRIC OXIDE-NUCLEOPHILE ADDUCTS USEFUL AS CARDIOVASCULAR AGENTS

[75] Inventors: Danae D. Christodoulou, Frederick; David A. Wink, Jr., Hagerstown; Larry K. Keefer, Bethesda, all of Md.

[73] Assignee: The United States of America as represented by the Department of Health and Human Services, Washington, D.C.

[21] Appl. No.: 858,885

[22] Filed: Mar. 27, 1992

[51] Int. Cl.$^6$ ............... A61K 31/28; C07F 13/00
[52] U.S. Cl. .................. 514/492; 514/494; 514/499; 514/906; 514/929; 556/45; 556/113; 556/130
[58] Field of Search ............... 556/45, 113, 130; 514/494, 499, 492, 906, 929

[56] References Cited

U.S. PATENT DOCUMENTS

| | | | |
|---|---|---|---|
| 3,153,094 | 10/1964 | Reilly | 260/576 |
| 4,954,526 | 9/1990 | Keefer | 514/611 |
| 5,039,705 | 8/1991 | Keefer et al. | 514/611 |

OTHER PUBLICATIONS

1991, Article by Maragos, et al., Complexes of .NO with Nucleophiles as Agents for the Controlled Biological Release of Nitric Oxide. Vasorelaxant Effects, Journal of Medicinal Chemistry, vol. 34, No. 11.

May 10, 1990, Article by Myers, et al., Vasorelaxant Properties of the Endothelium-Derived Relaxing Factor More Closely Resemble S-Nitrosocysteine than Nitric Oxide, Nature, vol. 345.

Jan. 1989, Article by Louis J. Ignarro, Endothelium-derived Nitric Oxide: Actions and Peroperties, The FASEB Journal, vol. 3.

1988, Article by Francis V. DeFeudis, Endothelium-Dependent Vasorelaxation—A New Basis For Developing Cardiovascular Drugs, Drugs of Today, vol. 24, No. 2, pp. 103–115.

Jun. 11, 1987, Article by Palmer, et al., Nitric Oxide Release Accounts for the Biological Activity of Endothelium-Derived Relaxing Factor, Nature, vol. 327.

1987, Article by Kruszyna, et al., Red Blood Cells Generate Nitric Oxide from Directly Acting, Nitrogenous Vasodilators, Toxicology and Applied Pharmacology 91, 429–438.

1986, Article by Lawrence A. Trissel, Intravenous Infusion Solutions, Handbook on Injectable Drugs, Fourth Addition.

1984, Article by Robert F. Furchgott, The Role of Endothelium in the Responses of Vascular Smooth Muscle to Drugs, Ann. Rev. PHARMOCOL TOXICOL, 24:175–97.

1982, Article by DeLuca, et al., Parenteral Drug-Delivery Systems, Pharmaceutics and Pharmacy Practice.

1982, Article by Hansen, et al., N-Nitrosation of Secondary Amines by Nitric Oxide Via the 'Drago Complex,' ARC Sci., Publ., pp. 21–29.

1981, Article by Ignarro, et al., Mechanism of Vascular Smooth Muscle Relaxation by Organic Nitrates, Nitrites, Nitroprusside and Nitric Oxide: Evidence for the Involvement of S-Nitrosothiols as Active Intermedi-
(List continued on next page.)

*Primary Examiner*—José G. Dees
*Assistant Examiner*—Porfirio Nazario
*Attorney, Agent, or Firm*—Leydig, Voit & Mayer, Ltd.

[57] ABSTRACT

Mixed ligand metal complexes of nitric oxide-nucleophile adducts, useful as cardiovascular agents of the formula KA, wherein A is $[(M)_x^{x'}(L)_y(R^1R^2N-N_2O_2)_x]$, and K is a pharmaceutically acceptable counterion present in the composition when the overall charge of A is not zero, counterion K being present only in an amount to neutralize A. Methods of treating mammals with such compounds are provided. Pharmaceutical compositions containing such compounds are also provided.

41 Claims, 1 Drawing Sheet

OTHER PUBLICATIONS ates, The Journal of Pharmacology and Experimental Therapeutics, vol. 218, No. 3.

1977, Article by Lutz, et al., Isolation of Trioxodinitrato (II) Complexes of Some First Row Transition Metal Ions, J.C.S. Chem.

Feb. 1963, Article by Longhi, et al., Metal-Containing Compounds of the Anion $(C_2H_5)_2NN_2O_2-$, Inorg. Chem., vol. 2.

1962, Article by Russell S. Drago, Reactions of Nitrogen (II) Oxide, Advances in Chemistry Series, No. 36.

Apr. 20, 1961, Article by Drago, et al., The Reaction of Nitrogen (II) Oxide with Various Primary and Secondary Amines, Journal of American Chem. Soc., vol. 83.

Jun. 1932, Article by Heinz Gehlen, Uber Reaktionen und Eigenschaften des Stickoxyds und seiner Verbindungen, II. Mitteil: Zur Kenntnis der Salze Der stickoxyd-schwefligen Säure, Aus d. Chem. Institut D. Universitat Konigsberg I. Pr., Eingegaugen am 1.

Jun. 1932, Article by Birckenbach, et al., Der Raman-- Effekt als Grundlage einer organischen Spektralanalyse (I. Mitteil.), Aus d. Chem. Institut D. Betgakademie Clausthal, Eingegaugen am 9.

*Chemical Abstracts*, 26, 4764–65, of Gehlen, "Über Reaktionen und Eigenschaften des Stickoxyds und seiner Verbindungen, II. Mitteil: Zur Kenntnis der Salze der stickoyd-schwefligen Säure" (Aus d. Chem. Institut D. Universität Königberg i Pr., Eingegangen am 1 Juni 1932), *Ber.*, 65B, 1130–40 (1932).

*Chemical Abstracts*, 28, 2636, of Weitz et al., "Zur Kenntniss der stickoxyd-schwefligen Säure (II. Mitteil)" (Aus d. Chem. Instituten d. Universitäten Halle u. Gleften, Eingegangen am 21 Oktober 1933), *Ber.*, 66B, 1718–27 (1933).

MIXED LIGAND METAL COMPLEXES OF NITRIC OXIDE-NUCLEOPHILE ADDUCTS USEFUL AS CARDIOVASCULAR AGENTS

BACKGROUND OF THE INVENTION

1. Field of the Invention

This invention relates to novel compounds useful as cardiovascular agents, to novel pharmaceutical compositions and to a novel method of treating cardiovascular disorders.

2. Description of the Prior Art

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol.Toxicol. 24, 175–197, 1984.) In 1987, Palmer et al., presented evidence that EDRF is identical to the simple molecule, nitric oxide, NO (Nature 317, 524–526, 1987), though more recently, that conclusion has been challenged (Myers et al., Nature, 345, 161–163, 1990). It has been hypothesized for years that many nitrovasodilators, which mimic the effect of EDRF, like glyceryl trinitrate, amyl nitrite, $NaNO_2$ and sodium nitroprusside (SNP), do so by virtue of their conversion to a common moiety, namely NO, which is also a vasodilator. (See Kruszyna et al., Tox. & Appl. Pharmacol., 91, 429–438, 1987; Ignarro, FASEB J. 3, 31–36, 1989; and Ignarro et al., J. Pharmacol. Exper. Therapeutics 218(3), 739–749, 1981.)

Numerous nitric oxide-nucleophile complexes have been described, e.g., Drago, *ACS Adv. Chem. Ser.*, Vol. 36, p. 143–149 (1962). See also R. Longhi and R. S. Drago, Inorg. Chem. 2 85, (1963). Some of these complexes are known to evolve nitric oxide on heating or hydrolysis, e.g., Hansen, et al., IARC SCI. PUBL., Vol. 41, p. 21–29 (1982).

Evidence that nitric oxide is released from the endothelial cells and is responsible for the relaxation of the vascular smooth muscle, and hence the control of blood pressure, has resulted in the development of artificial agents that can deliver nitric oxide in vivo. A very important class of such agents is the nitric oxide-nucleophile complexes. Recently, a method for treating cardiovascular disorders in a mammal with certain nitric oxide-nucleophile complexes has been disclosed in U.S. Pat. No. 4,954,526.

The cardiovascular agents described in U.S. Pat. No. 4,954,526 are complexes formed from nitric oxide and primary amines, and esters, ethers or other derivatives of the resulting adducts. These compounds spontaneously release nitric oxide in vivo, and it is this release which accounts for their biological activity. While these nitric oxide-nucleophile complexes have been found to exhibit biological activity through their release of nitric oxide, novel derivatives of these nitric oxide-nucleophile complexes which also release nitric oxide and which exhibit improved potency and/or stability would also be beneficial.

Thus, it is a principal object of the present invention to provide novel cardiovascular agents useful in treating cardiovascular disorders.

It is another object of the invention to provide novel cardiovascular agents with improved potency.

It is further object of the invention to provide novel cardiovascular agents with improved stability.

It is yet another object to provide pharmaceutical compositions suitable for use in the treatment of cardiovascular disorders.

It is also an object of the invention to provide a method for the treatment of cardiovascular disorders.

These and other objects and advantages will be apparent from the following description of the invention.

SUMMARY OF THE INVENTION

Figure 1:
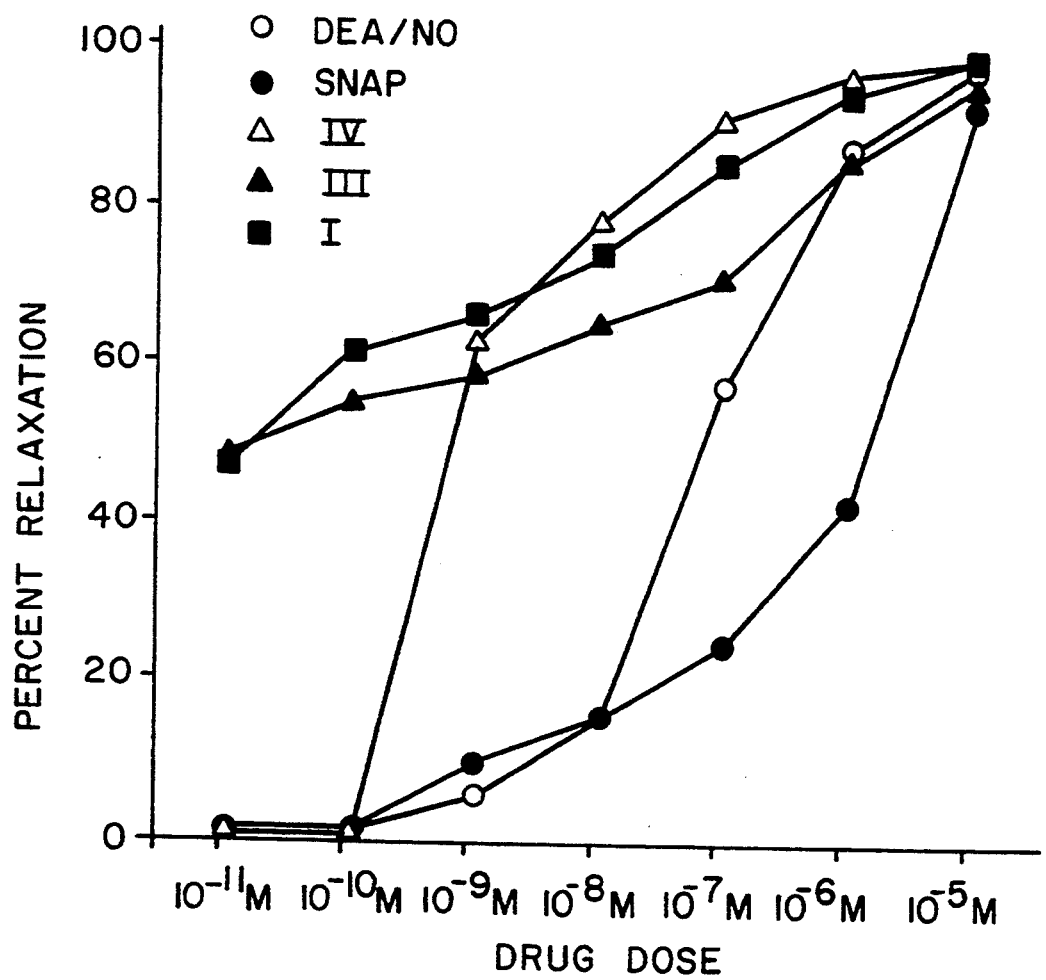
FIG. 1 is a dose response curve obtained from the Pharmacology Experiment described below.

In accordance with one aspect of the invention, there is provided a novel class of mixed ligand metal complexes of nitric oxide-nucleophile adducts. The compounds of the present invention are of various nuclearities, that is, they may contain one or more metal centers. In addition to the nitric oxide-nucleophile adduct ligands, the compounds also include secondary ligands. These ligands may be labile, and may thus be replaced by the donor atoms of a tissue component. Alternatively, these ligands may augment the affinity of the metal center for specific donor atoms of a tissue component, without becoming dissociated from the metal center. The metal centers coordinate both to the bidentate —$N_2O_2$ group and to the secondary ligands of the compositions.

The mixed ligand metal complexes of nitric oxide-nucleophile adducts of the present invention exhibit improved potency and/or stability in relation to other nitric oxide-nucleophile adducts. The compounds of the present invention are potent anti-hypertensives and thus are useful for treating cardiovascular disorders in which lowering the blood pressure has a beneficial result. It is believed that these compositions function by releasing NO in the blood and/or vascular tissue after injection. It is also believed that the unique properties of various metal centers are used to facilitate NO release from the compounds to the target tissue, either by way of reduction and oxidation pathways controlled by the metal center, or by interaction of the metal center with proteins through displacement of labile ligands from the metal center by donor atoms of the protein or through attachment of these donor atoms to vacant coordination sites in the compounds without prior ligand dissociation.

In accordance with another aspect of the present invention, a pharmaceutical composition which includes the mixed ligand metal complexes of nitric oxide-nucleophile adducts described herein is provided.

The present invention further provides a method for treating cardiovascular disorders by administering a therapeutically effective amount of a mixed ligand metal complex of nitric oxide-nucleophile adducts.

DETAILED DESCRIPTION OF THE PREFERRED EMBODIMENTS

The present invention provides novel compounds in which nitric oxide-nucleophile complex ligands are coordinated via the oxygen donor atoms of the bidentate —$N_2O_2$ functionality to metal centers which are, in turn, bound to one or more additional ligands. The compounds of this invention are capable of releasing nitric oxide. The compositions in accordance with the invention have the formula:

KA, wherein A is:

$[(M)_x{}^{x'}(L)_y R^1R^2N\text{-}N_2O_2)_z]$, and

M is a pharmaceutically acceptable metal, or where x is at least two, M may be a mixture of two different pharmaceutically acceptable metals;

L is a ligand, different from $(R^1R^2N\text{-}N_2O_2)$, and is bound to at least one metal;

$R^1$ and $R^2$ are each organic moieties and may be the same or different;

x is an integer of from 1 to 10, inclusive, and preferably from 1 to 4, inclusive;

x' is the formal oxidation state of the metal M, and is an integer of from 1 to 6 inclusive, and preferably from 1 to 3, inclusive;

y is an integer of from 1 to 18, inclusive, and preferably from 1 to 6 inclusive, and where y is at least two, L may be the same ligand or a mixture of different ligands.

z is an integer of from 1 to 20, inclusive, preferably from 2 to 10 inclusive;

provided that where M is copper, x is one, L is methanol and y is one, that at least one of $R^1$ or $R^2$ is not ethyl; and K is a pharmaceutically acceptable counterion present in the composition when the overall charge of A is not zero, counterion K being present only in an amount to neutralize A. It will thus be appreciated that where the overall charge of A is zero, the novel compositions of the present invention do not include the counterion K.

The metal center, M, is a pharmaceutically acceptable metal ion. The ligand $R^1R^2N\text{-}N_2O_2$ is coordinated to a metal center, M, via the oxygen donor atoms of the $-N_2O_2$ functional group. The secondary ligands L are coordinated to a metal center, M, via the donor atoms on the ligands L. The ligands L may be bridging and/or terminal ligands. The secondary ligands L may also be appended to either or both of $R^1$ and $R^2$ of the ligand $(R^1R^2N\text{-}N_2O_2)$. Examples of structures of compounds in accordance with this invention are shown in Examples 1–3 below. These structures were determined by x-ray crystallography.

The pharmaceutically acceptable metal center may be any of the number of pharmaceutically acceptable metals known to those skilled in the art. The only requirement for the pharmaceutically acceptable metal center chosen is biological compatibility in a mammal. Biologically acceptable metal centers include alkali metals such as sodium, potassium, lithium, and the like; alkaline earth metals such as calcium, magnesium, and the like; Group III metals such as aluminum; Group IV metals such as tin; and transition metals, including iron, copper, manganese, zinc, cobalt, vanadium, molybdenum, platinum and the like. Preferably, the metal center is copper, zinc, manganese or magnesium. Metals that may be considered toxic may, nevertheless, be pharmaceutically acceptable and thus within the scope of this invention if their complexes with nitric oxide-nucleophile adducts are sufficiently potent pharmacologically that the total concentration of the metal upon dosing is below the toxic threshold of the metal.

The secondary ligand L coordinates to the metal center M, and may be appended to either or both of $R^1$ and $R^2$ of the ligand $(R^1R^2N\text{-}N_2O_2)$. Where the metal complex includes more than one ligand L, the ligands may be the same, or they may be different.

While applicants do not wish to be bound by any particular theory, it is believed that the unexpected increase in potency of the mixed ligand metal complexes of nitric oxide-nucleophile adducts of the present invention is a result of the ability of the metal center M to interact with available sites on mammalian tissue. This interaction may be enhanced by the secondary ligand, L. Where the secondary ligand L is labile, it is believed that the ligand may be replaced by an active moiety from mammalian tissue. In that instance, it is believed that mixed ligand metal complexes of nitric oxide-nucleophile adducts interact with the target tissue. Interaction of the mixed ligand metal complexes of nitric oxide-nucleophile adducts with the target tissue potentially increases the local concentration of nitric oxide at the tissue of interest and therefore improves therapeutic response. In this aspect, it is thus believed that the secondary ligand L may be any chemical moiety that may be readily exchanged with donor atoms in mammalian tissue. However, it is believed that mixed ligand metal complexes of nitric oxide-nucleophile adducts wherein the secondary ligand L does not dissociate from the metal center are also active. It is believed that in compounds where the secondary ligand L does not dissociate from the metal center, the metal center M is coordinatively unsaturated such that donor atoms in mammalian tissue may bind to vacant sites in the coordination sphere of the metal. Release of nitric oxide from the metal complex is thus increased at the target tissue with consequent improvement in response.

The $(R^1R^2N\text{-}N_2O_2)$ ligand can coexist with other biologically important secondary ligands, L, in the secondary ligand metal complexes described herein. This is illustrated, for example in Example 3 below, the metal complex $Et_2NH_2{}^+[Cu_2(OAc)_3(Et_2N\text{-}N_2O_2)_2]^-$, wherein in the isolation and structural characterization of Et denotes the ethyl group, $CH_3CH_2$- and OAc denotes the acetate group, $CH_3C(O)O^-$.

In accordance with the invention, the secondary ligand L may be an alkyloxy having from one to 20 carbon atoms, a carboxylate having from one to 20 carbon atoms, an alcohol having from one to 20 carbon atoms, an amine, including primary, secondary and tertiary amines having from one to 20 carbon atoms, ethers having from one to 20 carbon atoms, esters having from one to 20 carbon atoms, amides having from one to 20 carbon atoms, sulfur- or phosphorus- containing ligands, substituted derivatives of the above named groups, or a halide, ammonia, aquo, hydroxo, and oxo ligands. The ligands may contain straight or branched chain or cyclic substituted organic moieties.

Alkyloxy includes, for example, methoxy, ethoxy, n-propoxy, and the like. Carboxylate includes, for example, acetoxy, 2-aminopropionoxy, oxalato, and the like. Alcohols include methanol, ethanol, phenol, and the like. Amines include spermine, porphyrins, pyridine, adenine, and the like. Ethers include tetrahydrofuran, crown ethers, and the like. Phosphorus-containing ligands include phosphate, nucleic acids, and the like. Sulfur-containing ligands include sulfhydryl or thiolate groups, sulfide or disulfide ligands, and the like. Amides include peptide groups, dimethylformamide, and the like.

$R^1$ and $R^2$, which may be the same or different, are organic moieties. $R^1$ and $R^2$ may be loweralkyl, aryl, or arylalkyl and either or both of $R^1$ and $R^2$ may be substituted by one to three substituents. The substituents may be the same or different, and may be selected from halo (i.e., fluorine, chlorine, bromine or iodine), hydroxy, substituted or unsubstituted alkoxy, amino, amido, ammonium or acyl.

By loweralkyl, it is meant straight chain and branched chain groups of one to twelve carbon atoms, inclusive, with the proviso that no branch occur on the alpha carbon of the alkyl groups. By straight chain alkyl is meant non-branched methyl, ethyl, n-propyl, n-butyl, n-hexyl, n-heptyl, n-octyl, n-decyl and like groups. By branched chain alkyl is meant groups such as 3-methylpentyl, 2-ethylhexyl, and like groups. The proviso means that groups like isopropyl or 1-methylbutyl are excluded. Alkyl groups having from two to six carbon atoms are preferred.

Aryl groups means substituted or unsubstituted phenyl, naphthyl, pyrrolyl, pyridinyl, quinolinyl, isoquinolinyl and the like. Arylalkyl means an alkyl group of one to three carbon atoms, substituted by an aryl group.

The groups $R^1$ and $R^2$ may, together with the nitrogen atom to which they are bonded, form a heterocyclic group. The heterocyclic group is preferably selected from the group consisting of

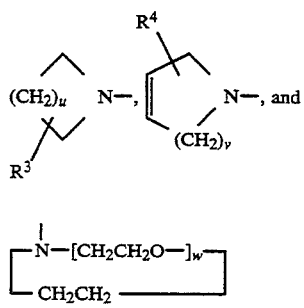

wherein u is 1 to 12, v is 1 to 3, w is 1 to 5, $R^3$ is hydrogen, a straight chain alkyl group having from one to eighteen carbon atoms, inclusive, a branched chain alkyl group having from three to six carbon atoms, inclusive, a cycloalkyl group having from three to eight carbon atoms, inclusive, phenyl or tolyl, and $R^4$ is hydrogen, a straight chain alkyl group having from one to six carbon atoms, inclusive, or a branched chain alkyl group having from three to six carbon atoms, inclusive. Of the $R^1R^2N$- heterocyclic groups encompassed by the formulas set forth above, there are mentioned, for example, azetidino, pyrrolidino, piperidino, azacylooctyl, substituted piperidino (e.g., 2-methyl, 3-methyl, 4-methyl, 2-ethyl, 4-phenyl, 2-propyl, 4-propyl and 4-tert.-butylpiperidino), substituted pyrrolidino (e.g., 2-methyl and 3-methylpyrrolidino), 1,2,3,6-tetrahydropyridino, 3-pyrrolino, morpholino, 1-aza-9-crown-3, 1-aza-12-crown-4, 1-aza-15-crown-5 and 1-aza18-crown-6. Morpholino is a preferred $R^1R^2N$- moiety. Many commercially available nitrogen-containing heterocyclic compounds can be used to prepare compounds, wherein $R^1R^2N$- is a heterocyclic moiety.

K is a pharmaceutically acceptable counterion present in the composition when the overall charge of A is not zero, counterion K being present only in an amount to neutralize A. K may be either a cation or an anion, depending on whether A is negatively or positively charged, respectively. Thus, by way of example, K may be a cation, including alkali metal ions, ammonium or substituted ammonium ions, alkaline earth metal ions, and the like or K may be an anion, including halide, nitrate, nitrite, hydroxide, carbonate, bicarbonate, phosphate, tetrafluoroborate, hexafluorophosphate, and tetraphenylboron anions and the like.

The mixed ligand metal complexes of nitric oxide-nucleophile adducts described herein are potent antihypertensives. These compositions are significantly more potent than nitric oxide-nucleophile complexes previously known. Their potency is improved by over an order of magnitude. The compositions of this invention are useful for lowering the blood pressure and treating any cardiovascular disorder in which lowering the blood pressure will have a beneficial effect. The invention provides an effective method of lowering the blood pressure by administering the compound to a mammal.

By way of illustration, and not in limitation, the compounds of the present invention may be synthesized by reacting a compound of the formula $Q^+(R^1R^2N$-$N_2O_2)^-$ where Q is sodium or diethylammonium, with metal ions in the presence of a solvent which may provide the secondary ligand. Synthesis and isolation of the compounds is preferably conducted in dry, non-aqueous solvents under anaerobic conditions which prolong the half lives of the ligands $(R^1R^2N$-$N_2O_2)^-$ and of the products. In general, refrigerated storage is recommended to prolong shelf life.

The following Examples are illustrative of, and not in limitation of, the present invention.

EXAMPLE

This example illustrates the preparation of $Cu_2$-$(OCH_2CH_3)_2((CH_3CH_2)_2N$-$N_2O_2)_2$, which has the following structure:

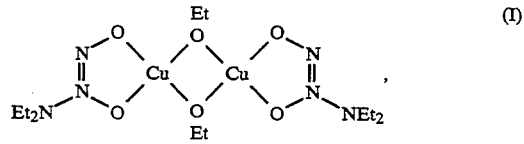

(I)

wherein Et denotes the ethyl group, $CH_3CH_2$-.

In this synthesis, 1.5 g (9.6 mmol) $Na(CH_3CH_2)_2N$-$N_2O_2$ was dissolved in 30 ml dried and degassed methanol at $-20°$ C. To that solution, a solution of 1.09 g (6.3 mmol) $CuCl_2.2H_2O$ in 20 ml methanol was transferred via cannula. The resulting dark blue solution was stirred under argon for 30 min. The solvent was removed by vacuum distillation while the solution was kept cold. In a Dri-Lab glove box, the residue was extracted with a total of 50 ml absolute ethanol and filtered. The blue filtrate was further concentrated to a third of the volume, while keeping the solution at $-20°$ C. This solution was refrigerated at $-30°$ C., under argon. The product was precipitated out in the form of blue prisms over a period of a week and was isolated under inert atmosphere by removing the supernatant solution and washing the crystals with hexane. Yield: 0.88 g, 57%.

Calculated for $C_{12}H_3ON_6O_6Cu_2$ (mol wt 481) C, 29.93; H,6.23; N, 17.46; Cu, 26.40.

Found: C,29.84; H,6.11; N,17.42; Cu, 26.69.

In the compound of this Example the group A as defined by the general formula is neutral, so there is no counterion, K.

EXAMPLE 2

This example illustrates the preparation of Cu₃(OCH₃)₄((CH₃CH₂)₂N-N₂O₂)₂·2[Cu₂(OCH₃)₂((CH₃CH₂)₂N-N₂O₂)₂, having the structure:

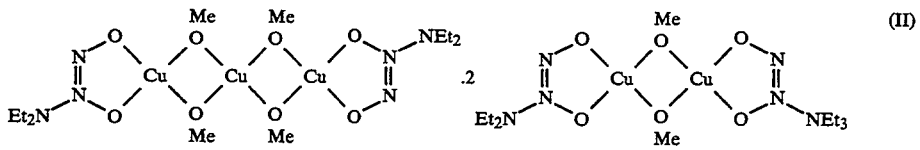

wherein Et denotes the ethyl group CH₃CH₂-, and Me denotes the methyl group CH₃-.

This product was obtained by transformation of the dinuclear species of Example 1 in methanol at −30° C. The composition of Example 1, 0.18 g (0.37 mmol), was dissolved in 20 ml methanol at room temperature, i.e., 25° C., under inert atmosphere. The blue solution was filtered and allowed to stand at −30° C. under argon, and over a period of two weeks the mixed species (II) was crystallized out. The mixed composition (II) was isolated from the cold solution by removing the supernatant liquid, washed with hexane, and dried under inert atmosphere. Yield: 77 mg, 49%.

Calculated for C₃₂H₈₄N₈O₂₀Cu₇ (mol wt 1484.5) C, 25.87; H, 5.65; N, 16.97; Cu, 29.94.

Found: C, 25.92; H, 5.69; N, 16.68; Cu, 30.88.

In the compound of this Example, the group, A, as defined by the general formula is neutral, so there is no counterion, K.

EXAMPLE 3

This example illustrates the preparation of (CH₃CH₂)₂NH₂⁺[Cu₂(OCOCH₃)₃((CH₃CH₂)₂N-N₂O₂)₂], which has the structure:

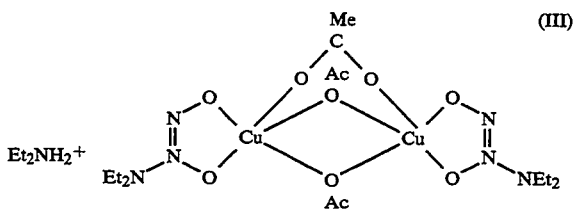

wherein Me denotes the methyl group, CH₃-, Et denotes the ethyl group, CH₃CH₂-, and Ac denotes the acetyl group, CH₃C(O)-.

In this synthesis, 0.54 g (2.6 mmol) (CH₃CH₂)₂NH₂⁺((CH₃CH₂)₂N-N₂O₂)⁻ was dissolved in 20 ml dry and degassed acetonitrile at −50° C. To that solution, a solution of 0.51 g (2.6 mmol) Cu(CH₃C(O)O)₂·H₂O in 20 ml solvent (acetonitrile) was transferred via cannula. The resulting blue solution was stirred for one hour and the solvent was removed under vacuum at −30° C. The concentrated solution (~5 ml) was filtered cold under inert atmosphere in a Dri-Lab glove box. The blue filtrate was allowed to stand at −30° C. under argon. The product was precipitated out over a period of ten days, and was isolated from the cold solution by removal of the supernatant liquid under inert atmosphere. The translucent green-blue crystals were washed with two portions of diethyl ether and dried. Yield: 0.22 g, 26%.

Calculated for C₁₈H₄₁N₇O₁₀Cu₂ (mol wt 642) C, 33.64; H, 6.38; N, 15.26; Cu, 19.78.

Found: C, 33.56; H, 6.28; N, 15.19; Cu, 19.98.

In the compound of this Example, the group, A, as defined by the general formula is negatively charged, so the compound includes counterion K, which is (Et₂NH₂⁺).

EXAMPLE 4

This example illustrates the preparation of Cu(CH₃OH)((CH₃CH₂)₂N-N₂O₂)₂, which has the following structure:

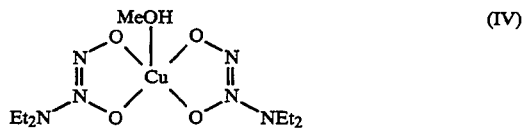

wherein Et denotes the ethyl group, CH₃CH₂-, and MeOH denotes methanol.

In this synthesis, 0.47 g (1 mmol) Cu₂(OCH₂CH₃)₂((CH₃CH₂)₂N-N₂O₂)₂ was dissolved in 20 ml dried and degassed methanol at −20° C. To that solution, a solution of 0.20 g (2 mmol) KOAc in 20 ml of MeOH was added. The resulting bright blue solution was cooled, concentrated to one half of the volume and filtered. The blue filtrate was allowed to stand at −30° C., under argon, for one week. The product was precipitated out as blue chunks and it was isolated from the cold solution by removing the supernatant liquid under inert atmosphere. The product was washed with hexane and dried. Yield: 0.14 g, 40%.

Calculated for C₉H₃₄N₆O₅Cu (mol wt 359.5) C, 30.04; H, 6.67; N, 23.36: Cu, 17.66.

Found: C, 29.11; H, 6.56; N, 22.79; Cu, 18.47.

In the compound of this Example, the group, A, as defined by the general formula is neutral so the compound does not include counterion K.

EXAMPLE 5

This Example illustrates the preparation of a secondary ligand metal complex of a nitric oxide-nucleophile adduct in accordance with the invention wherein the secondary ligand L is appended to R¹ of the ligand (R¹R²N-N₂O₂). In this Example, py denotes the group 2-pyridyl, and Me denotes the methyl group.

In this Example, [pyCH₂CH₂NH₂Me]⁺·[pyCH₂CH₂N(Me)N₂O₂]⁻, 1.0 g (3 mmol), was dissolved in methanol at −20° C. To that solution was added a solution of 0.42 g (1.6 mmol) vanadyl acetylacetonate [VO(acac)₂] in methanol. The color changed from pale green-blue to olive green. The reaction mixture was concentrated to a green oil. By two successive recrystallizations of the oil from acetonitrile, the white by-product, (pyCH₂CH₂NH₂Me⁺)(acac⁻), was removed. The green oil is a compound believed to have the formula:

PHARMACOLOGY EXPERIMENT

The vasorelaxant activity of the compositions of the present invention was tested using a standard isolated vascular ring preparation.

In the test procedures utilized, thoracic aortic rings from New Zealand White rabbits were suspended in pH 7.4 buffer at 37° C and a 10 g preload was applied to each. After equilibration for 2 hours, the rings were preconstricted with norepinephrine. By measuring the grams of relaxation induced by adding the complexes to the organ baths at successively increasing concentrations from $10^{-11}$ to $10^{-5}$ M, a dose-response curve was constructed for each compound as shown in FIG. 1.

In FIG. 1,

-o- is DEA/NO, namely, $Na((CH_3CH_2)_2N-N_2O_2)$;

- - is SNAP, namely, S-nitroso-N-acetylpenicillamine, an S-nitrosothiol reported to be vasoactive and akin structurally to compounds claimed by Myers et al. (loc. cit., Nature, 345, 161–163, 1990) to be the EDRF;

-Δ- is the compound of Example 4, namely, $Cu(CH_3OH)((CH_3CH_2)_2N-N_2O_2)_2$ (structure IV, above),

- - is the compound of Example 3, namely, $(CH_3CH_2)_2NH_2{}^+[Cu_2(OAc)_3((CH_3CH_2)_2N-N_2O_2)_2]^-$ (structure III above);

- - is the compound of Example 1, namely, $Cu_2(OCH_2CH_3)_2((CH_3CH_2)_2N-N_2O)_2$ (structure I, above).

It can be seen from these data that the mixed ligand metal complexes of nitric oxide-nucleophile adducts of the present invention, namely the compounds of Examples 1 and 3, are significantly more potent than DEA/NO and SNAP.

Thus the potency of the free $(R^1R^2N-N_2O_2)$ ion, as reflected in the DEA/NO data, is increased sustantially by binding it to a metal ion in mixed ligand metal complexes such as I and III above. The compounds I and III are also substantially more potent than SNAP, which it has been suggested is a close structural relative of the endogenous EDRF.

It was also found that the compound of Example 4 is more potent than DEA/NO and SNAP.

PHARMACEUTICAL COMPOSITIONS

The novel mixed ligand metal complexes of nitric oxide-nucleophile adducts in accordance with the invention and the compound of Example 4 are useful for treating any cardiovascular disorder that will respond favorably to a decrease in blood pressure. These disorders include chronic hypertension, hypertensive crisis (an acute hypertensive emergency), acute congestive heart failure, angina, acute myocardial infarction, left ventricular failure, cerebrovascular insufficiency and intracranial hemorrhage. The compositions may be particularly advantageous for treating acute disorders such as hypertensive crisis, toxemia of pregnancy and acute congestive heart failure. The compositions may be administered by any suitable route, e.g., by injection, inhalation, and oral administration. The preferred method of administration is by injection into the blood system, most preferably by intravenous injection. The chronic disorders can be treated by continuous intravenous infusion.

The pharmaceutical compositions of the invention are comprised of the mixed ligand metal complexes of nitric oxide-nucleophile adducts and a pharmaceutical carrier. The carrier can be any of those conventionally used and is limited only by chemico-physical considerations such as solubility and lack of reactivity with the compound and by the route of administration. For intravenous administration, the carrier may be aqueous and may contain solubilizing agents, buffers, preservatives, antioxidants, chelating agents, and agents to control the toxicity, such as dextrose or sodium chloride. The requirements for effective pharmaceutical carriers for injectable compositions are well known by those of ordinary skill in this art. (See "Pharmaceutics and Pharmacy Practice" J. B. Lippincott Company, Philadelphia, 1982, edited by Banker and Chalmer, pages 238–250, which are incorporated by reference; see also ASHP "Handbook on Injectable Drugs," 4th edition by Trissel, pages 622–630, which lists commercially available intravenous infusion solutions, and which pages are also incorporated by reference.) The compounds may also be formulated as inclusion complexes, such as, for example, cyclodextrin inclusion complexes; or the compounds may be carried within liposomes. Preferred pharmaceutical carriers for injection are PBS (phosphate buffered saline), 5% dextrose and sterile water. Since the compounds of the present invention and the compound of Example 4 are subject to being oxidized by oxygen, an antioxidant, such as ascorbate, can be added to the carrier to increase the shelf-life.

In the case of oral preparations, the compounds may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents. The amount of the compound to be used in a pharmaceutical composition of course varies according to the type of cardiovascular disorder encountered and the route of administration chosen. A suitable dosage is thought to be about 0.01 to 10.0 mg/kg/day body weight where hypertension, atherosclerosis, cerebral vasospasm or coronary vasospasm is being treated and the route of administration is intravenous. The preferred dosage is of course that amount just sufficient to treat a particular cardiovascular disorder and would preferably be an amount from about 0.05 to 5.0 mg/kg/day.

We claim:

1. A compound of the formula:

KA wherein A is:
$[(M)_x{}^{x'}(L)_y(R^1R^2N-N_2O_2)_z]$, and

M is a pharmaceutically acceptable metal, or where x is at least two, a mixture of two different pharmaceutically acceptable metals;

L is a ligand bound to at least one metal selected from the group consisting of $C_1$–$C_{20}$ alkoxy, $C_1$–$C_{20}$ carboxylate, $C_1$–$C_{20}$ alcohol, amino, $C_1$–$C_{20}$ alkyl amine, $C_1$–$C_{20}$ ether, $C_1$–$C_{20}$ ester, $C_1$–$C_{20}$ amide, a sulfur- or phosphorus- containing ligand, a substituted derivative of any of the above, a halide, ammonia, an aquo, a hydroxo and an oxo ligand;

$R^1$ and $R^2$ may be the same or different and are selected from the group consisting of loweralkyl, aryl, and arylalkyl;

x is an integer of from 1 to 10, inclusive;

x' is the formal oxidation state of the metal M, and is an integer of from 1 to 6 inclusive;

y is an integer of from 1 to 18, inclusive, and where y is at least 2, the ligands L may be the same or different.

z is an integer of from 1 to 20, inclusive;

with the first proviso that where M is copper, x is one, L is methanol and y is one, that at least one of $R^1$ or $R^2$ is not ethyl; and the second proviso that where L is aquo and x is one, that M is not sodium, potassium, calcium or nickel; and K is a pharmaceutically acceptable counterion present in the composition when the overall charge of A is not zero, counterion K being present only in an amount to neutralize A.

2. The compound of claim 1, wherein M is selected from the group consisting of Group III metals, Group IV metals and transition metals.

3. The compound of claim 2 wherein $R^1$ and $R^2$ together with the nitrogen atom to which they are bonded form a heterocyclic group.

4. The compound of claim 2, wherein the metal M is selected from the group consisting of copper, zinc, and manganese, x is an integer of 1 to 4, inclusive, L is a member selected from the group consisting of alkoxy, carboxylate, alcohol and amine, y is an integer of from 1 to 6 inclusive, $R^1$ and $R^2$ are selected from the group consisting of loweralkyl, and z is an integer of from 2 to 10, inclusive.

5. The compound of claim 4, wherein the metal is selected from the group consisting of zinc and manganese.

6. The compound of claim 4, wherein at least one ligand L is appended to at least one of $R^1$ and $R^2$.

7. A method for treating cardiovascular disorders, said method comprising administering to a mammal a therapeutically effective amount of a compound of the formula:

KA, wherein A is:

$[(M)_x{}^{x'}(L)_y(R^1R^2N-N_2O_2)_z]$, and

M is a pharmaceutically acceptable metal, or where x is at least two, a mixture of two different pharmaceutically acceptable metals;

L is a ligand bound to at least one metal selected from the group consisting of $C_1$–$C_{20}$ alkoxy, $C_1$–$C_{20}$ carboxylate, $C_1$–$C_{20}$ alcohol, amine, $C_1$–$C_{20}$ alkyl amine, $C_1$–$C_{20}$ ether, $C_1$–$C_{20}$ ester, $C_1$–$C_{20}$ amide, a sulfur- or phosphorus- containing ligand, a substituted derivative of any of the above, a halide, ammonia, an aquo, a hydroxo and an oxo ligand;

$R^1$ and $R^2$ may be the same or different and are selected from the group consisting of loweralkyl, aryl, and arylalkyl;

x is an integer of from 1 to 10, inclusive;

x' is the formal oxidation state of the metal M, and is an integer of from 1 to 6 inclusive;

y is an integer of from 1 to 18, inclusive, and where y is at least 2, the ligands L may be the same or different;

z is an integer of from 1 to 20, inclusive;

with the first proviso that where M is copper, x is one, L is methanol and y is one, that at least one of $R^1$ or $R^2$ is not ethyl; and the second proviso that where L is aquo and x is one, that M is not sodium, potassium, calcium or nickel; and K is a pharmaceutically acceptable counterion present in the composition when the overall charge of A is not zero, counterion K being present only in an amount to neutralize A.

8. The method of claim 7 wherein the metal M is selected from the group consisting of Group III metals, Group IV metals and transition metals.

9. The method of claim 8, wherein $R^1$ and $R^2$ together with the nitrogen atom to which they are bonded form a heterocyclic group.

10. The method of claim 8, wherein the metal M is selected from the group consisting of copper, zinc, and manganese, x is an integer of 1 to 4, inclusive, L is a member selected from the group consisting of alkoxy, carboxylate, alcohol and amine, y is an integer of from 1 to 6 inclusive, $R^1$ and $R^2$ are selected from the group consisting of loweralkyl, and z is an integer of from 2 to 10, inclusive.

11. The method of claim 10, wherein the metal is selected from the group consisting of zinc and manganese.

12. The method of claim 10, wherein at least one ligand L is appended to at least one of $R^1$ and $R^2$.

13. The method of claim 8, wherein said compound is administered by intravenous injection.

14. A pharmaceutical composition for treating cardiovascular disorders comprising a therapeutically effective amount of a composition of the formula:

KA, wherein A is:

$[(M)_x{}^{x'}(L)_6(R^1R^2N-N_2O_2)_z]$,

M is a pharmaceutically acceptable metal, or where x is at least two, a mixture of two different pharmaceutically acceptable metals;

L is a ligand bound to at least one metal selected from the group consisting of $C_1$–$C_{20}$ alkoxy, $C_1$–$C_{20}$ carboxylate, $C_1$–$C_{20}$ alcohol amine, $C_1$–$C_{20}$ alkyl amine, $C_1$–$C_{20}$ ether, $C_1$–$C_{20}$ ester, $C_1$–$C_{20}$ amide, a sulfur- or phosphorus- containing ligand, a substituted derivative of the above, a halide, ammonia, an aquo, a hydroxo and an oxo ligand;

$R^1$ and $R^2$ may be the same or different and are selected from the group consisting of loweralkyl, aryl, and arylalkyl x is an integer of from 1 to 10, inclusive;

x' is the formal oxidation state of the metal M, and is an integer of from 1 to 6 inclusive;

y is an integer of from 1 to 18, inclusive, and where y is at least 2, the ligands L may be the same or different;

z is an integer of from 1 to 20, inclusive;

with the first proviso that where M is copper, x is one, L is methanol and y is one, that at least one of $R^1$ or $R^2$ is not ethyl; and the second proviso that where L is aquo and x is one, that M is not sodium, potassium, calcium or nickel; and K is a pharmaceutically acceptable counterion present in the composition when the overall charge of A is not zero, counterion K being present only in an amount to neutralize A.

15. The pharmaceutical composition of claim 14, wherein the metal M is selected from the group consisting of Group III metals, Group IV metals, and transition metals.

16. The pharmaceutical composition of claim 15, wherein $R^1$ and $R^2$ together with the nitrogen atom to which they are bonded form a heterocyclic group.

17. The pharmaceutical composition of claim 15, wherein the metal M is selected from the group consisting of copper, zinc, and manganese, x is an integer of 1 to 4, inclusive, L is a member selected from the group consisting of alkoxy, carboxylate, alcohol and amine, y is an integer of from 1 to 6 inclusive, $R^1$ and $R^2$ are selected from the group consisting of loweralkyl, and z is an integer of from 2 to 10 inclusive.

18. The pharmaceutical composition of claim 17, wherein the metal is selected from the group consisting of zinc and manganese.

19. The pharmaceutical composition of claim 17, wherein at least one ligand L is appended to at least one of $R^1$ and $R^2$.

20. The pharmaceutical composition of claim 14, wherein said composition is suitable for intravenous injection.

21. The compound of claim 1, wherein the metal M is selected from the group consisting of alkali metals, alkaline earth metals, Group III metals, Group IV metals and transition metals.

22. The compound of claim 21 wherein $R^1$ and $R^2$ together with the nitrogen atom to which they are bonded form a heterocyclic group.

23. The compound of claim 21, wherein the metal M is selected from the group consisting of copper, zinc, manganese and magnesium, x is an integer of 1 to 4, inclusive, L is a member selected from the group consisting of alkoxy, carboxylate, alcohol and amine, y is an integer of from 1 to 6 inclusive, $R^1$ and $R^2$ are selected from the group consisting of loweralkyl, and z is an integer of from 2 to 10, inclusive.

24. The compound of claim 23, wherein the metal is selected from the group consisting of zinc, manganese and magnesium.

25. The compound of claim 23, wherein at least one ligand L is appended to at least one of $R^1$ and $R^2$.

26. The compound of claim 1, wherein the metal M is selected from the group consisting of magnesium, Group III metals, Group IV metals and transition metals except for nickel; and $R^1$ and $R^2$ are selected from the group consisting of loweralkyl, aryl and arylalkyl.

27. The compound of claim 26 wherein $R^1$ and $R^2$ together with the nitrogen atom to which they are bonded form a heterocyclic group.

28. The method of claim 7 wherein the metal M is selected from the group consisting of alkali metals, alkaline earth metals, Group III metals, Group IV metals and transition metals.

29. The method of claim 28, wherein $R^1$ and $R^2$ together with the nitrogen atom to which they are bonded form a heterocyclic group.

30. The method of claim 28, wherein the metal M is selected from the group consisting of copper, zinc, manganese and magnesium, x is an integer of 1 to 4, inclusive, L is a member selected from the group consisting of alkoxy, carboxylate, alcohol and amine, y is an integer of from 1 to 6 inclusive, $R^1$ and $R^2$ are selected from the group consisting of loweralkyl, and z is an integer of from 2 to 10, inclusive.

31. The method of claim 30, wherein the metal is selected from the group consisting of zinc, manganese and magnesium.

32. The method of claim 30, wherein at least one ligand L is appended to at least one of $R^1$ and $R^2$.

33. The method of claim 7 wherein the metal M is selected from the group consisting of magnesium, Group III metals, Group IV metals and transition metals except for nickel.

34. The method of claim 33, wherein $R^1$ and $R^2$ together with the nitrogen atom to which they are bonded form a heterocyclic group.

35. The pharmaceutical composition of claim 14, wherein the metal M is selected from the group consisting of alkali metals, alkaline earth metals, Group III metals, Group IV metals, and transition metals.

36. The pharmaceutical composition of claim 35, wherein $R^1$ and $R^2$ together with the nitrogen atom to which they are bonded form a heterocylic group.

37. The pharmaceutical composition of claim 35, wherein the metal M is selected from the group consisting of copper, zinc, manganese and magnesium, x is an integer of 1 to 4, inclusive, L is a member selected from the group consisting of alkoxy, carboxylate, alcohol and amine, y is an integer of from 1 to 6 inclusive, $R^1$ and $R^2$ are selected from the group consisting of loweralkyl, and z is an integer of from 2 to 10 inclusive.

38. The pharmaceutical composition of claim 37, wherein the metal is selected from the group consisting of zinc, manganese and magnesium.

39. The pharmaceutical composition of claim 37, wherein at least one ligand L is appended to at least one of $R^1$ and $R^2$.

40. The pharmaceutical composition of claim 14, wherein the metal M is selected from the group consisting of magnesium, Group III metals, Group IV metals, and transition metals except for nickel; and $R^1$ and $R^2$ are selected from the group consisting of loweralkyl, aryl and arylalkyl.

41. The pharmaceutical composition of claim 40, wherein $R^1$ and $R^2$ together with the nitrogen atom to which they are bonded form a heterocylic group.

* * * * *